United States Patent [19]

Costes et al.

[11] 4,072,728

[45] Feb. 7, 1978

[54] PROCESS FOR THE PREPARATION OF 1,2-DICHLOROETHANE IN TWO REACTION ZONES BY REACTING CHLORINE WITH NOT MORE THAN 102 MOLE PERCENT OF ETHYLENE

[75] Inventors: Jean-Raymond Costes, Dampierre; Jean-Claude Strini, St-Auban; Serge Hardouin, Lyon, all of France

[73] Assignee: Rhone-Progil, France

[21] Appl. No.: 617,409

[22] Filed: Sept. 29, 1975

Related U.S. Application Data

[63] Continuation of Ser. No. 427,375, Dec. 21, 1973, abandoned.

[30] Foreign Application Priority Data

Dec. 27, 1972 France .................................. 72.46389

[51] Int. Cl.$^2$ ....................... C07C 17/02; C07C 17/10
[52] U.S. Cl. ................................. 260/660; 260/652 P; 260/654 S
[58] Field of Search ................. 260/660, 652 P, 654 S

[56] References Cited

U.S. PATENT DOCUMENTS

| 2,356,785 | 8/1944 | Hammond ................. 260/652 P X |
| 2,746,999 | 5/1956 | Gunkler et al. ................. 260/660 |
| 3,475,504 | 10/1969 | Wircher et al. ................. 260/658 |
| 3,691,239 | 9/1972 | Hackett et al. ................. 260/652 P |

FOREIGN PATENT DOCUMENTS 960,083  6/1964  United Kingdom ................. 260/660

*Primary Examiner*—Floyd D. Higel

[57] ABSTRACT

An improved process for the production of 1,2-dichloroethane in which chlorine and ethylene are reacted in the liquid phase in the absence of light and in the presence of a Lewis acid catalyst wherein all of the chlorine used in the reaction and a fraction of the total ethylene within the range of 90 to 100 mole percent based upon the total chlorine are introduced to a first homogeneous agitated reaction zone, the products from the first zone are passed to a second homogeneous agitated reaction zone into which there is also introduced the remaining ethylene in countercurrent flow to the flow of the 1,2-dichloroethane, with the total amount of ethylene introduced not exceeding 102 mole percent of the total chlorine.

9 Claims, No Drawings

PROCESS FOR THE PREPARATION OF 1,2-DICHLOROETHANE IN TWO REACTION ZONES BY REACTING CHLORINE WITH NOT MORE THAN 102 MOLE PERCENT OF ETHYLENE

This is a continuation application of Ser. No. 427,375, filed Dec. 21, 1973, now abandoned.

The present invention relates to a liquid phase process for the production of 1,2-dichloroethane.

Many processes for the industrial preparation of 1,2-dichloroethane from ethylene and chlorine are known. The most widespread comprise reacting chlorine and gaseous ethylene within the 1,2-dichloroethane reaction product, which is kept in a liquid condition, in the presence of a catalyst which, in most cases, is ferric chloride.

In order to restrict the formation of undesired higher chlorinated substances such as 1,1,2-trichloroethane, to fairly low values in the vicinity of 1%, it is necessary to operate at a temperature lower than 100° C. and more particularly lower than 60° C., and to meter the introduction of the gases so as to observe the stoichiometry of the reaction. The introduction operation is generally effected in a single reaction vessel, the gases flowing in the same direction. This method suffers from two serious disadvantages. As the ethylene is much less soluble in the reaction liquid than the chlorine, the ethylene tends to escape therefrom before it has completely reacted with the chlorine. The result is a loss of ethylene from 2 to 6% of the amount used, and this is very substantial drop from the point of view of material, and therefore from the economic point of view, in high-capacity installations. Moreover, the 1,2-dichloroethane produced contains up to about 2 g per kg of dissolved chlorine. This presents a danger in subsequent operations since, on the one hand, it can be entrained by the discharges from the reaction vessel and can explode upon contact with ethylene and hydrogen (which is a frequent impurity in industrial chlorine). Moreover, the dissolved chlorine is particularly corrosive and, finally, it causes atmospheric pollution.

In the known processes, the conventional way of meeting the dangers presented by the dissolved chlorine is to move substantially away from the stoichiometric amounts, by using an excess of ethylene in the reaction zone, for example a $C_2H_4/Cl_2$ molar ration of from 1.03 to 1.05, which results in a gaseous effluent which contains from 20 to 40% by volume of ethylene, the result of which is a greater loss of ethylene, but without completely eliminating the dissolved chlorine. Thus, in order completely to remove chlorine, it is necessary to wash the 1,2-dichloroethane produced with a basic solution. This, however, is a very inconvenient operation as the ferric chloride which was used to catalyze the reaction is subject to severe flocculation at the interface of the washing means, and interferes with the separation of 1,2-dichloroethane from the washing waters. Moreover, using such an excess of ethylene suffers from the disadvantage of promoting in particular the formation of 1,1,2-trichloroethane, detrimentally affecting the degree of selectivity of 1,2-dichloroethane.

It is an object of the present invention to overcome the foregoing disadvantages, and it is a more specific object of the invention to provide a process for the industrial preparation of 1,2-dichloroethane in which pollution due to release of unreacted chlorine and ethylene is significantly reduced or eliminated.

In accordance with the process of the invention, the reaction of chlorine and ethylene is carried out at a temperature of from 20° to 80° C. and more particularly from 40° to 70° C., protected from light radiation, in liquid 1,2-dichloroethane containing a Lewis acid, and preferably ferric chloride, dissolved in two successive homogeneous reactions zones which are perfectly agitated and which are contained in a single reaction vessel. All the chlorine used and only a fraction of the ethylene required, from 90 to 100 molar percent and preferably from 97 to 99.5% based on the total chlorine, are continuously introduced into the first homogenous reaction zone; the resulting products are passed into the second homogeneous reaction zone into which the other fraction of ethylene is continuously introduced in counterflow to a flow of liquid 1,2-dichloroethane, so that the total of the two amounts of ethylene introduced represents from 100 to 102% and preferably from 100.1 to 101% of the total chlorine.

It has been found that the 1,2-dichloroethane produced in and issuing from the second homogeneous reaction zone is virtually free from dissolved chlorine which can be discovered by analysis, and that the gases which escape from the second reaction zone, after condensation of the vapors of 1,2-dichloroethane which is entrained, contain a proportion which is lower than 10% by volume and more particularly less than 5% by volume of ethylene. Thus, the ethylene loss is greatly reduced and does not exceed 1% of the total amount of ethylene. It has also been found that the formation of by-products is very greatly reduced, as will appear from the following examples.

According to the invention, the two reaction zones are so arranged that the gases discharging from the first homogeneous reaction zone are immediately brought into contact with the 1,2-dichloroethane contained in the second homogeneous reaction zone, so that there is no possibility of uncontrolled reactions between the various constituents of the gaseous effluents (vapors of 1,2-dichloroethane, $C_2H_4$, $C_2H_6$, $CH_4$, $HCl$, $O_2$, $CO$, $CO_2$, $H_2$, $N_2$).

In accordance with one embodiment of the invention, the temperature maintained in the first reaction zone is lower by from 2° to 60° C. and preferably by from 5° to 25° C., than that in the second zone.

In accordance with another embodiment of the invention, the ratio between the volume of the first zone and that of the second zone is from 1 to 10 and more particularly from 1.2 to 3.

In accordance with a particular embodiment of the invention, interposed between the first and second reaction zones is a diaphragm and/or a wickerwork-like assembly and/or a baffle deflector assembly and/or a distributor means.

In a particular form of the invention, the gases from the second zone are washed with water, the 1,2-dichloroethane produced by the present process is subjected to liquid-liquid extraction of the Lewis acid, by means of the acid water which results therefrom.

The chlorine used can be either in liquid form which is gasified before reaction, or in gaseous form in the raw state such as is collected at the outlets of chlorine manufacturing works. The efficiency of conversion of chlorine to 1,2-dichloroethane is not changed, but only and very slightly the efficiency of conversion of ethylene, whether use is made of liquid chlorine in a state of 99.9% purity or a chlorine in a state of 88–98% purity, the main impurities being $CO_2$, $O_2$, $N_2$, $H_2$, and $CO$. These gases are inert under the operating conditions of the reaction.

It was found that pressure did not have any marked influence on the chlorination reactions which occur in the reaction vessel.

Having described the basic concepts of the invention, reference is now made to the following examples which are provided by way of illustration, but not of limitation, of the practice of the invention.

EXAMPLE 1

The following are continuously introduced into the first reaction zone whose volume is 18 m³, which is perfectly agitated by circulation by means of an external pump, and in counterflow to the 1,2-dichloroethane which is circulating, being maintained at 60° C. and containing 200 parts per million of dissolved ferric chloride at 60° C:

1114 kg per hour of ethylene in a state of 99% by volume purity (impurities: $C_2H_6$, $CH_4$), 2880 kg per hour of chlorine in a state of 94% by volume purity (impurities: $0_2$, $H_2$, $CO_2$, $N_2$), that is to say, 99.5 molar percent of ethylene with respect to the total amount of pure chlorine.

The gaseous and liquid flows from the first zone pass through a distributor means into the second homogeneous zone whose volume is 8 m³ and which is perfectly agitated, in the same reaction vessel. These flows react with 10 kg per hour of ethylene (that is to say, 0.9 molar percent of the total of pure chlorine) which is injected into the second zone continuously in counterflow to the circulating flow of liquid 1,2-dichloroethane. The temperature is approximately 65° C. in the second zone.

At the outlet from the reaction vessel, the liquid 1,2-dichloroethane produced does not contain any dissolved chlorine which can be discovered when testing with potassium iodide.

The discharge gases are cooled to 5° C. in order to recover the 1,2-dichloroethane by condensation. A proportion of ethylene of about 5% by volume is observed in the discharges after condensation. They are then passed to a water-absorption column. The resulting acid water with a pH value of 2.5 is used for washing the 1,2-dichloroethane produced.

The production of 1,2-dichloroethane is 3960 kg per h, which contains 300 parts per million by weight of 1,1,2-trichloroethane and three parts per million by weight of ferric chloride.

The corresponding ethylene loss is 0.4% with respect to the ethylene used, and the chlorine loss is lower than 0.01%.

By way of comparison, Example 1 was repeated, but in an uncompartmented reaction vessel, having a single homogeneous zone with the same total volume of 26 m³.

The following are introduced into the reaction zone in counterflow to the circulation of 1,2-dichloroethane:

1160 kg per hour of ethylene in a state of 99% purity, 2900 kg per hour of chlorine in a state of 94% purity, which corresponds to 103 molar percent of ethylene with respect to the amount of total chlorine.

The proportion of ethylene in the discharges is observed to be 25% by volume (after recovery of the 1,2-dichloroethane by condensation).

At the outlet from the reaction vessel, the 1,2-dichloroethane produced then contains 0.7 g of dissolved chlorine per kg. In order to remove this, it is washed with a 6% by weight liquid solution of sodium hydroxide. This washing operation consumes 2.5 kg per hour of caustic soda.

The production of 1,2-dichloroethane is 3930 kg per hour, containing 1500 parts per million by weight of 1,1,2-trichloroethane.

The ethylene loss is approximately 3% of the amount used, while the chlorine loss is 0.1% with respect to the total amount of chlorine.

It should be noted that a comparative test using the total hourly flow rates of ethylene and chlorine corresponding to those used in Example 1 but in a reaction vessel which has a single homogeneous zone cannot be carried out, because of the fact that the proportions of effluent gases comprising $C_2H_4$, $Cl_2$, and $H_2$ in the discharged gases would be in the ranges likely to cause an explosion.

EXAMPLE 2

The following are introduced into the first zone, with a volume of 19.5 m³, of a reaction vessel of the type used in Example 1:

1484 kg per hour of ethylene in a state of 99% by volume purity, 3920 kg per hour of chlorine in a state 95% by volume purity, that is to say, 97 molar percent of ethylene with respect to the total amount of pure chlorine.

The temperature in the first homogeneous reaction zone is maintained at about 63° C., and the amount of ferric chloride dissolved in the 1,2-dischloroethane is 180 parts per million by weight.

The products from the reaction in the first zone are passed, as in Example 1, into the second homogeneous zone, with a volume of 6.5 m³, into which 51 kg per hour of ethylene, that is to say, 3.4 molar percent of the total amount of chlorine, is continuously introduced, in counterflow to the circulating flow of liquid 1,2-dichloroethane.

The temperature in the second zone is about 70° C.

The liquid 1,2-dichloroethane produced at the outlet of the reaction vessel does not contain any dissolved chlorine which can be discovered upon testing with potassium iodide.

After cooling of the discharge gases to 3° C. in order to recover the 1,2-dichloroethane by condensation, the proportion of ethylene observed in the discharge gases is about 5% by volume. The discharge gases are then washed in a water-absorption column. The resulting acid water which has a pH value of 3, is used for washing the 1,2-dichloroethane produced.

The ethylene loss corresponds to 0.4% with respect to the ethylene used, while the chlorine loss is lower than 0.01%.

The production of 1,2-dichloroethane is 5360 kg per hour, containing 340 parts per million by weight of 1,1,2-trichloroethane and less than 3 parts per million by weight of ferric chloride.

EXAMPLE 3

Example 1 above is repeated, except that the amount of ethylene introduced into the first zone is 1086 -kg, which represents 97 molar percent of ethylene with respect to the total amount of chlorine, while into the second zone is introduced 38 kg per hour of ethylene, namely 3.5 molar percent of the total amount of chlorine.

The same production of 1,2-dichloroethane is obtained, and the ethylene loss is the same as in Example 1. The 1,2-dichloroethane produced contains 350 parts per million by weight of 1,1,2-trichloroethane, and less than 3 parts per million by weight of ferric chloride.

It will be understood that various changes and modifications can be made in the details of formulation, procedure, and apparatus without departing from the spirit of the invention.

We claim:

1. In a process for the production of 1,2-dichloroethane in which chlorine and ethylene are reacted at a temperature within the range of 20° to 80° C in the absence of light radiation and in the presence of a Lewis acid catalyst and liquid 1,2-dichloroethane, the improvement comprising continuously introducing to a first homogeneous agitated reaction zone of 1,2-dichloroethane all of the chlorine used in the reaction and a fraction of the total ethylene within the range of 90 to 100 mole percent based on the total amount of chlorine, immediately passing the resulting products from the first zone to a second homogeneous, agitated reaction zone, introducing to the second zone the remaining ethylene countercurrently to the flow of 1,2-dichloroethane, with the total amount of ethylene introduced to the first and second zones not exceeding 102 mole percent of the total chlorine used and with both reaction zones being included in a single vessel, and recovering 1,2-dichloroethane from the second zone while venting not more than 1 mole percent of the ethylene based upon the total amount of ethylene introduced.

2. A process according to claim 1 wherein the fraction of the ethylene introduced to the first zone is from 97 to 99.5 molar percent of the total amount of chlorine is continuously introduced into the first homogeneous zone and the other fraction is introduced into the second homogeneous zone, such that the total of the two amounts of ethylene introduced to the first and second zones from 100.1% to 101% of the total amount of chlorine.

3. A process according to claim 1 wherein the temperature maintained in the first reaction zone is lower by from 2° to 60° C. than that in the second reaction zone.

4. A process according to claim 1 wherein the ratio between the volume of the first zone and that of the second zone is from 1 to 10.

5. A process according to claim 1 wherein the gases from the second zone are washed with water to produce an acid water, and the 1,2-dichloroethane produced is treated for liquid-liquid extraction of the Lewis acid with said acid water.

6. A process as according to claim 1 wherein a distributor means is interposed between the first and second homogeneous zones.

7. In a process for the production of 1,2-dichloroethane in which chlorine and ethylene are reacted at a temperature within the range of 20° to 80° C in the absence of light and in the presence of a Lewis acid catalyst and in the presence of liquid 1,2-dichloroethane, the improvement comprising continuously introducing to a first homogeneous agitated reaction zone of 1,2-dichloroethane all of the chlorine used in the reaction, said chlorine containing impurities including at least one of carbon dioxide, oxygen, nitrogen, hydrogen and carbon monoxide, and a fraction of the total ethylene within the range of 90 to 100 mole percent based on the total amount of chlorine, immediately passing the resulting products from the first zone to a second homogeneous agitated reaction zone, introducing to the second zone the remaining ethylene countercurrently to the flow of 1,2-dichloroethane, with the total amount of ethylene introduced to the first and second zones not exceeding 102 mole percent of the total chlorine used and with both reaction zones being included in a single vessel, and recovering 1,2-dichloroethane while venting from the second zone a mixture of ethylene and the impurities in the chlorine, with the ethylene constituting not more than one mole percent of the total ethylene supplied to the reaction zones based upon the total amount of ethylene introduced.

8. In a process for the production of 1,2-dichloroethane in which chlorine and ethylene are reacted at a temperature within the range of 20° to 80° C in the absence of light radiation and in the presence of a Lewis acid catalyst and liquid 1,2-dichloroethane, the improvement comprising continuously introducing to a first homogeneous agitated reaction zone of 1,2-dichloroethane all of the chlorine used in the reaction and a fraction of the total ethylene within the range of 90 to 100 mole percent based on the total amount of chlorine, immediately passing the resulting products from the first zone through distributor means to a second homogeneous, agitated reaction zone, introducing to the second zone the remaining ethylene countercurrently to the flow of 1,2-dichloroethane, with the total amount of ethylene introduced to the first and second zones not exceeding 102 mole percent of the total chlorine used and with both reaction zones being included in a single vessel, and recovering 1,2-dichloroethane from the second zone while venting not more than 1 mole percent of the ethylene based upon the total amount of ethylene introduced.

9. In a process for the production of 1,2-dichloroethane in which chlorine and ethylene are reacted at a temperature within the range of 20° to 80° C in the absence of light and in the presence of a Lewis acid catalyst and in the presence of liquid 1,2-dichloroethane, the improvement comprising continuously introducing to a first homogeneous agitated reaction zone of 1,2-dichloroethane all of the chlorine used in the reaction, said chlorine containing impurities including at least one of carbon dioxide, oxygen, nitrogen, hydrogen and carbon monoxide, and a fraction of the total ethylene within the range of 90 to 100 mole percent based on the total amount of chlorine, immediately passing the resulting products from the first zone through distributor means to a second homogeneous agitated reaction zone, introducing to the second zone the remaining ethylene countercurrently to the flow of 1,2-dichloroethane, with the total amount of ethylene introduced to the first and second zones not exceeding 102 mole percent of the total chlorine used and with both reaction zones being included in a single vessel, and recovering 1,2-dichloroethane while venting from the second zone a mixture of ethylene and the impurities in the chlorine, with the ethylene constituting not more than one mole percent of the total ethylene supplied to the reaction zones based upon the total amount of ethylene introduced.

* * * * *